(12) United States Patent
Stryer

(10) Patent No.: US 6,361,937 B1
(45) Date of Patent: *Mar. 26, 2002

(54) COMPUTER-AIDED NUCLEIC ACID SEQUENCING

(75) Inventor: Lubert Stryer, Stanford, CA (US)

(73) Assignee: Affymetrix, Incorporated, Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/618,834

(22) Filed: Mar. 19, 1996

(51) Int. Cl.[7] ............. C12Q 1/68; G01N 33/48; G01N 33/50; G01N 15/00
(52) U.S. Cl. ............. 435/6; 422/68.1; 702/19; 702/20
(58) Field of Search ............. 435/6; 536/24.3; 364/496, 497; 436/94; 935/76, 77; 702/19, 20; 422/68.1

(56) References Cited

U.S. PATENT DOCUMENTS

| | | | |
|---|---|---|---|
| 4,741,043 A | 4/1988 | Bacus | 382/6 |
| 4,965,725 A | 10/1990 | Rutenberg | 364/413.1 |
| 5,002,867 A | 3/1991 | Macevicz | 435/6 |
| 5,143,854 A | 9/1992 | Pirrung et al. | 436/518 |
| 5,200,313 A * | 4/1993 | Carrico | 435/6 |
| 5,202,231 A | 4/1993 | Drmanac et al. | 435/6 |
| 5,235,626 A | 8/1993 | Flamholz et al. | 378/34 |
| 5,273,632 A | 12/1993 | Stockham et al. | 204/180.1 |
| 5,288,514 A | 2/1994 | Ellman | 427/2 |
| 5,384,261 A | 1/1995 | Winkler et al. | 436/518 |
| 5,445,934 A | 8/1995 | Fodor et al. | 435/6 |
| 5,470,710 A | 11/1995 | Weiss et al. | 435/6 |
| 5,492,806 A | 2/1996 | Drmanac et al. | 435/5 |
| 5,503,980 A * | 4/1996 | Cantor | 435/6 |
| 5,525,464 A | 6/1996 | Drmanac et al. | 435/6 |
| 5,527,681 A | 6/1996 | Holmes | 435/6 |
| 5,733,729 A * | 3/1998 | Lipshutz et al. | 435/6 |

FOREIGN PATENT DOCUMENTS

| | | |
|---|---|---|
| WO | 8910977 | 11/1989 |
| WO | 9210092 | 6/1992 |
| WO | 9210588 | 6/1992 |
| WO | 9511995 | 5/1995 |
| WO | WO 95/35505 | 12/1995 |

OTHER PUBLICATIONS

Fodor, et al., Light–Directed, Spatially Addressable Parallel Chemical Synthesis, Science, vol. 251, Feb. 15, 1991, p 767–773.

Brown, et al., An Inexpensive MSI/LSI Mask Making System, Proceedings of 1981 Univ. Govt. Indus. Microelec. Symposium, May 26–27, 1981, pp. III–31 through III–38.

Dear, et al., A Sequence Assembly and Editing Program for Efficient Management of Large Projects, Nucleic Acids Research, vol. 19, No. 14, 1991 Oxford Univ. Press, pp. 3907–3911.

Drmanac et al., "DNA sequencing determination by hybridization: a strategy for efficient large scale sequencing," 1993, Science 260 1649–1652.

(List continued on next page.)

Primary Examiner—Ardin H. Marschel
(74) Attorney, Agent, or Firm—Ritter, Lang & Kaplan LLP

(57) ABSTRACT

A computer system for sequencing nucleic acids is provided. The computer system may be used for de novo sequencing of a nucleic acid sequence by analyzing the fluorescence intensities of hybridized nucleic acid probes on biological chips. The probes with the highest intensities are utilized to sequence the nucleic acid and related probes are analyzed to increase the accuracy of nucleic acid sequencing. The sequence of the nucleic acid sequence may be determined from hybridization intensities that do not allow identification of perfectly complementary probes.

42 Claims, 7 Drawing Sheets

OTHER PUBLICATIONS

Strezoska et al., "DNA sequencing by hybridization: 100 base read by a non-gel based method," 1991, PNAS 88 10089–1093.

Southern et al., "Analyzing and comparing nucleic acid sequences by hybridization to arrays of oligonucleotides: Evaluation using experimental models," 1992, Genomics 13 1008–1017.

Drmanac et al., "An algorithm for the DNA sequencing generation form k–Tuple word contents of the minimal number of random fragments," 1991, J. of Biomolecular Structure & Dynamics 8 1085–1102.

Drmanac, "Doctoral dissertation," Beograd, 1988. (English translation enclosed).

"Designer PCR™," Aug. 11, 1994, Advertisement from Research Genetics, Nucleic Acids Research, vol. 22, No. 15.

"Does your sequence analysis program offer the features and flexibility you need?" Jan. 11, 1993, Team Associates Inc., Nucleic Acids Research, vol. 21, No. 1.

Dierick et al., "Incorporation of dITP or 7–deaza dGTP during PCR improves sequencing of the product," Sep. 11, 1993, Nucleic Acids Research, Col. 21, No. 18, pp. 4427–4428.

Frech et al., "Computer assisted prediction, classification, and delimitation of protein binding sites in nucleic acids," Apr. 11,1993, Nucleic Acids Research, vol. 21, No. 7, pp. 1655–1664.

* cited by examiner

COMPUTER-AIDED NUCLEIC ACID SEQUENCING

COPYRIGHT NOTICE

A portion of the disclosure of this patent document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

SOFTWARE APPENDICES

Software Appendices A and B comprising six (6) sheets are included herewith.

BACKGROUND OF THE INVENTION

The present invention relates to the field of computer systems. More specifically, the present invention relates to computer systems for sequencing biological molecules including nucleic acids.

Devices and computer systems for forming and using arrays of materials on a substrate are known. For example, PCT application Ser. Nos. WO92/10588 and 95/11995, incorporated herein by reference for all purposes, describe techniques for sequencing or sequence checking nucleic acids and other materials. Arrays for performing these operations may be formed in arrays according to the methods of, for example, the pioneering techniques disclosed in U.S. Pat. Nos. 5,445,934 and 5,384,261, and U.S. patent application Ser. No. 08/249,188, each incorporated herein by reference for all purposes.

According to one aspect of the techniques described therein, an array of nucleic acid probes is fabricated at known locations on a chip or substrate. A labeled nucleic acid is then brought into contact with the chip and a scanner generates an image file (also called a cell file) indicating the locations where the labeled nucleic acids are bound to the chip. Based upon the image file and identities of the probes at specific locations, it becomes possible to extract information such as the nucleotide or monomer sequence of DNA or RNA. Such systems have been used to form, for example, arrays of DNA that may be used to study and detect mutations relevant to genetic diseases, cancers, infectious diseases, HIV, and other genetic characteristics.

The VLSIPS™ technology provides methods of making very large arrays of oligonucleotide probes on very small chips. See U.S. Pat. No. 5,143,854 and PCT patent publication Nos. WO 90/15070 and 92/10092, each of which is incorporated by reference for all purposes. The oligonucleotide probes on the DNA probe array are used to detect complementary nucleic acid sequences in a sample nucleic acid of interest (the "target" nucleic acid).

For sequence checking applications, the chip may be tiled for a specific target nucleic acid sequence. For example, the chip may contain probes that are perfectly complementary to the target sequence and probes that differ from the target sequence by a single base mismatch. These probes are tiled on a chip in rows and columns of cells, where each cell includes multiple copies of a particular probe. Additionally, "blank" cells may be present on the chip which do not include any probes. As the blank cells contains no probes, labeled targets should not bind specifically to the chip in this area. Thus, a blank cell provides a measure of the background intensity.

For de novo sequencing applications, the chip may include all the possible probes of a specific length. These probes are synthesized on the chip at known locations, typically with multiple copies of a particular probe in a cell. Blank cells may also be utilized to provide a measure of the background intensity.

SUMMARY OF THE INVENTION

The present invention provides an improved computer-aided system for sequencing sample nucleic acid sequences from nucleic acid hybridization information. The accuracy of nucleic acid sequencing is increased by analyzing the hybridization strength of related probes, where the related probes are identified according to mismatch information among the probes. The related probes may include single base mismatches or otherwise have identical subsequences. The methods of the present invention allow sequencing under conditions that do not allow identification of all of the probes that are perfectly complementary to part of the target nucleic acid sequence.

According to one aspect of the present invention, a computer system is used to sequence a nucleic acid by a method including the steps of: inputting hybridization intensities for a plurality of nucleic acid probes, the nucleic acid probes hybridizing with the nucleic acid sequence under conditions that do not allow identification of all of nucleic acid probes that are perfectly complementary to part of the nucleic acid sequence; and sequencing the nucleic acid sequence according to selected nucleic acid probes.

According to another aspect of the present invention, a computer system is used to sequence a nucleic acid by a method including the steps of: inputting hybridization intensities for a plurality of nucleic acid probes; selecting nucleic acid probes with highest numbers of single base mismatch neighbors among the probes, a single base mismatch neighbor being another probe that has the same sequence except for a single base that is different; and sequencing the nucleic acid sequence according to the selected nucleic acid probes.

According to another aspect of the present invention, a computer system is used to sequence a nucleic acid by a method including the steps of: inputting hybridization intensities for a plurality of nucleic acid probes; selecting nucleic acid probes that have fewer than a predetermined number of base mismatches with another probe; and sequencing the nucleic acid sequence according to the selected nucleic acid probes.

According to another aspect of the present invention, a nucleic acid is sequenced by a method including the steps of: contacting a set of oligonucleotide probes of predetermined sequence and length with the nucleic acid under hybridization conditions that do not allow differentiation between (i) those probes of the set which are perfectly complementary to part of the nucleic acid and (ii) those probes that are not perfectly complementary to part of the nucleic acid; selecting a subset of oligonucleotide probes that includes probes that are perfectly complementary to part of the nucleic acid and probes that are not perfectly complementary to part of the nucleic acid; and determining the sequence of the nucleic acid by compiling overlapping sequences of the subset of probes.

A further understanding of the nature and advantages of the inventions herein may be realized by reference to the remaining portions of the specification and the attached drawings.

BRIEF DESCRIPTION OF THE DRAWINGS

FIG. 8 shows a straight mismatch matrix for use with the process of FIG. 7; and

FIG. 9 shows an offset mismatch matrix for use with the process of FIG. 7.

DESCRIPTION OF THE PREFERRED EMBODIMENTS

Introduction

In the description that follows, the present invention will be described in reference to a Sun Workstation in a UNIX environment. The present invention, however, is not limited to any particular hardware or operating system environment. Instead, those skilled in the art will find that the systems and methods of the present invention may be advantageously applied to a variety of systems, including IBM personal computers running MS-DOS or Microsoft Windows. Therefore, the following description of specific systems are for purposes of illustration and not limitation.

Figure 1:
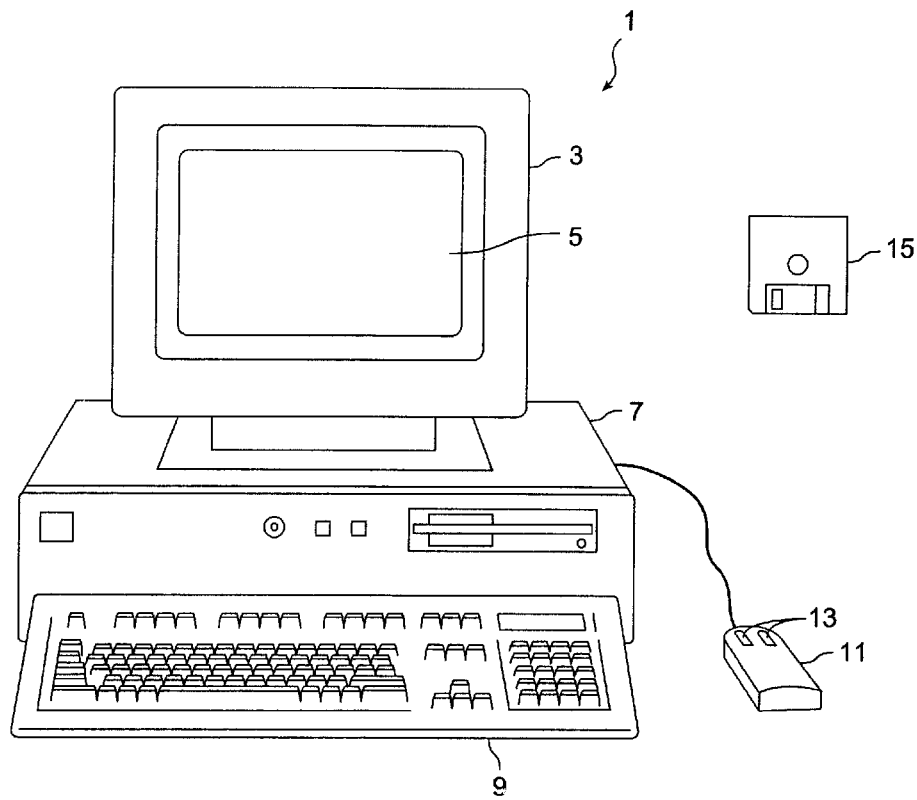
FIG. 1 illustrates an example of a computer system used to execute the software of the present invention.

FIG. 1 illustrates an example of a computer system used to execute the software of the present invention. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a floppy disk drive 14 and a hard drive (not shown) that may be utilized to store and retrieve software programs including computer or software code incorporating the present invention. Although a floppy disk 15 is shown as the computer readable storage medium, other computer readable storage media including CD-ROM, DRAM, hard drives, flash memory, tape, and the like may be utilized. Cabinet 7 also houses familiar computer components (not shown) such as a processor, memory, and the like.

Figure 2:
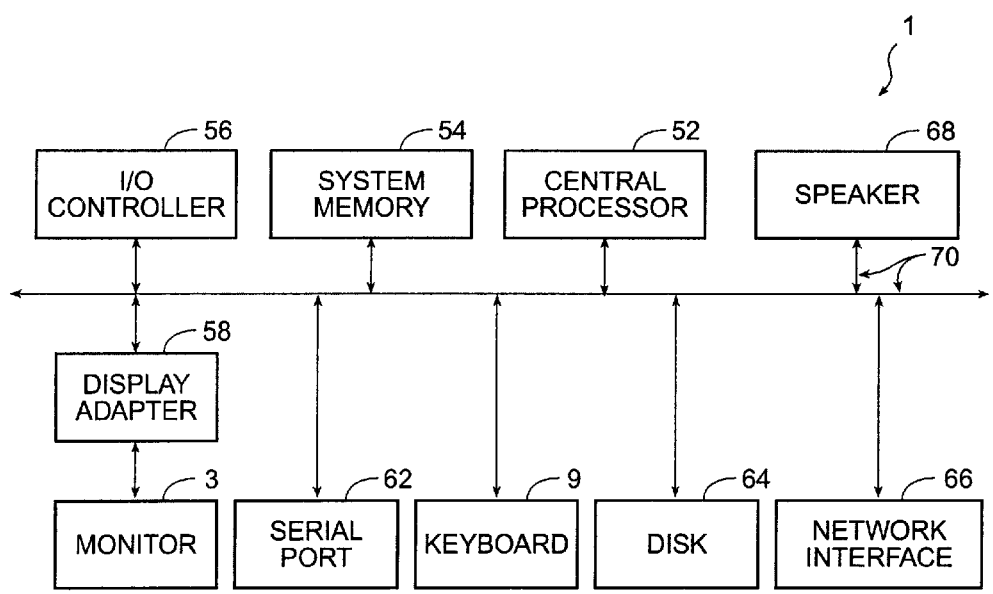
FIG. 2 shows a system block diagram of a typical computer system used to execute the software of the present invention.

FIG. 2 shows a system block diagram of computer system 1 used to execute the software of the present invention. As in FIG. 1, computer system 1 includes monitor 3 and keyboard 9. Computer system 1 further includes subsystems such as a central processor 52, system memory 54, I/O controller 56, display adapter 58, serial port 62, disk 64, network interface 66, and speaker 68. Disk 64 is representative of an internal hard drive, floppy drive, CD-ROM, flash memory, tape, or any other storage medium. Other computer systems suitable for use with the present invention may include additional or fewer subsystems. For example, another computer system could include more than one processor 52 (i.e., a multi-processor system) or memory cache.

Arrows such as 70 represent the system bus architecture of computer system 1. However, these arrows are illustrative of any interconnection scheme serving to link the subsystems. For example, speaker 68 could be connected to the other subsystems through a port or have an internal direct connection to central processor 52. Computer system 1 shown in FIG. 2 is but an example of a computer system suitable for use with the present invention. Other configurations of subsystems suitable for use with the present invention will be readily apparent to one of ordinary skill in the art.

The present invention provides methods of analyzing hybridization intensity files for a chip containing hybridized nucleic acid probes. In a representative embodiment, the files represent fluorescence data from a biological array, but the files may also represent other data such as radioactive intensity, light scattering, refractive index, conductivity, electroluminescence, or large molecule detection data. Therefore, the present invention is not limited to analyzing fluorescence measurements of hybridizations but may be readily utilized to analyze other measurements of hybridization.

For purposes of illustration, the present invention is described as being part of a computer system that designs a chip mask, synthesizes the probes on the chip, labels the nucleic acids, and scans the hybridized nucleic acid probes. Such a system is fully described in U.S. patent application Ser. No. 08/249,188 which has been incorporated by reference for all purposes. However, the present invention may be used separately from the overall system for analyzing data generated by such systems.

Figure 3:
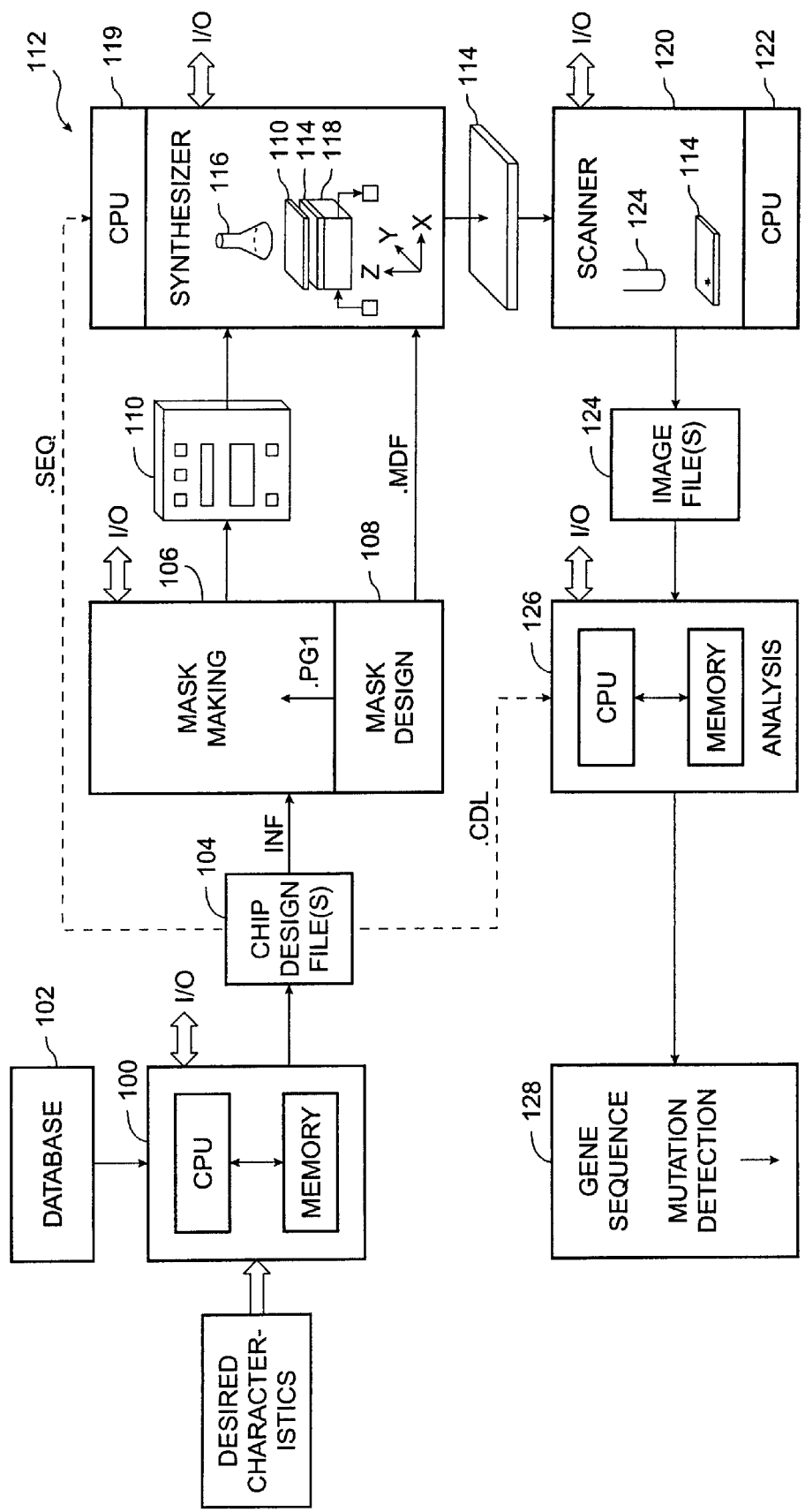
FIG. 3 illustrates an overall system for forming and analyzing arrays of biological materials such as DNA or RNA.

FIG. 3 illustrates a computerized system for forming and analyzing arrays of biological materials such as RNA or DNA. A computer 100 is used to design arrays of biological polymers such as RNA or DNA. The computer 100 may be, for example, an appropriately programmed Sun Workstation or personal computer or workstation, such as an IBM PC equivalent, including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application Ser. No. WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site, but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescein label (indicated by an asterisk in FIG. 3) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled target (*) has bound to the substrate. The output of scanner 120 is an image file(s) 124 indicating, in the case of fluorescein labeled target, the fluorescence intensity (photon counts or other related measurements, such as voltage) as a function of position on the substrate. Since higher photon counts will be observed where the labeled target has bound more strongly to the array of polymers (e.g., DNA probes on the substrate), and since the monomer sequence of the polymers on the substrate is known as a function of position, it becomes possible to determine the sequence(s) of polymer(s) on the substrate that are complementary to the target.

The image file 124 is provided as input to an analysis system 126 that incorporates the visualization and analysis methods of the present invention. Again, the analysis system may be any one of a wide variety of computer system(s), but in a preferred embodiment the analysis system is based on a Sun Workstation or equivalent. The present invention provides various methods of analyzing the chip design files and the image files, providing appropriate output 128. The present invention may further be used to identify specific mutations in a target such as DNA or RNA.

Figure 4:
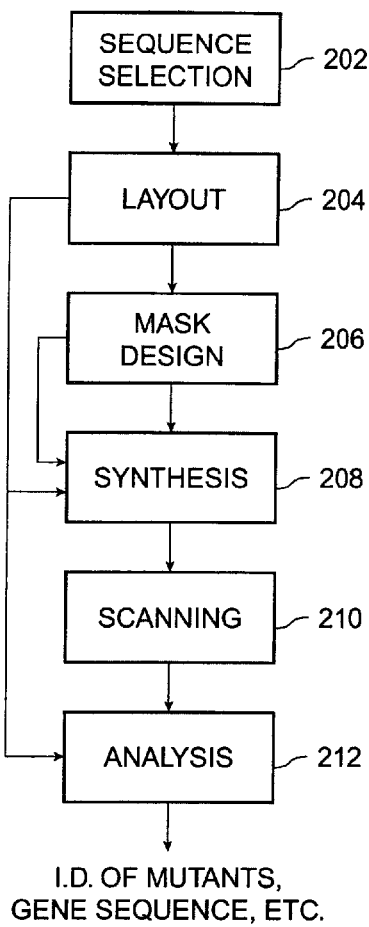
FIG. 4 is an illustration of the software for the overall system.

FIG. 4 provides a simplified illustration of the overall software system used in the operation of one embodiment of the invention. As shown in FIG. 4, in some cases (such as sequence checking systems) the system first identifies the genetic sequence(s) or targets that would be of interest in a particular analysis at step 202. The sequences of interest may identify a virus, microorganism or individual. Additionally, the sequence of interest may provide information about genetic diseases, cancers or infectious diseases. Sequence selection may be provided via manual input of text files or may be from external sources such as GenBank. In a preferred embodiment that performs de novo sequencing of target nucleic acids, this steps is not necessary as the chip includes all the possible n-mer probes (where n represents the length of the nucleic acid probe).

For de novo sequencing, a chip may be synthesized to include cells containing all the possible probes of a specific length. For example, a chip may be synthesized that includes all the possible 8-mer DNA probes. Such a chip would have 65,536 cells (4*4*4*4*4*4*4*4), with each cell corresponding to a particular probe. A chip may also include other probes including all the probes of other lengths.

At step 204 the system determines which probes would be desirable on the chip, and provides an appropriate "layout" on the chip for the probes. The layout implements desired characteristics such as an arrangement on the chip that permits "reading" of genetic sequence and/or minimization of edge effects, ease of synthesis, and the like.

Again referring to FIG. 4, at step 206 the masks for the synthesis are designed. At step 208 the software utilizes the mask design and layout information to make the DNA or other polymer chips. This software 208 will control, among other things, relative translation of a substrate and the mask, the flow of desired reagents through a flow cell, the synthesis temperature of the flow cell, and other parameters. At step 210, another piece of software is used in scanning a chip thus synthesized and exposed to a labeled target. The software controls the scanning of the chip, and stores the data thus obtained in a file that may later be utilized to extract sequence information.

At step 212 a computer system according to the present invention utilizes the layout information and the fluorescence information to evaluate the hybridized nucleic acid probes on the chip. Among the important pieces of information obtained from DNA probe arrays are the identification of mutant targets and determination of the genetic sequence of a particular target.

Figure 5:
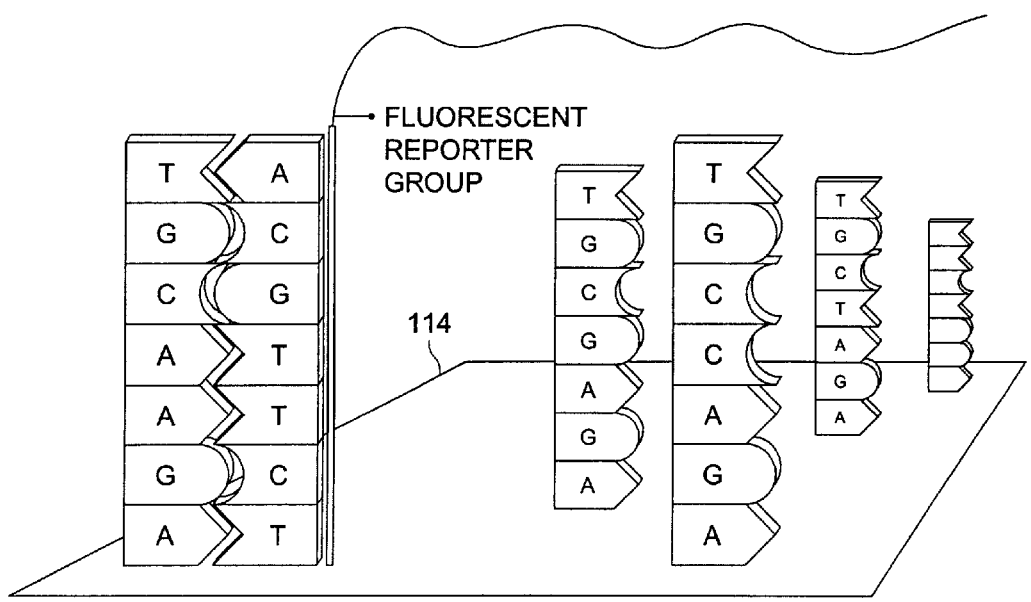
FIG. 5 illustrates conceptually the binding of probes on chips.

FIG. 5 illustrates the binding of a particular target DNA to an array of DNA probes 114. As shown in this simple example, the following probes are formed in the array:

```
3'-AGAACGT

AGACCGT

AGAGCGT

AGATCGT

.

.

.
```

As shown, when the fluorescein-labeled (or otherwise marked) target 5'-TCTTGCA is exposed to the array, it is complementary only to the probe 3'-AGAACGT, and fluorescein will be primarily found on the surface of the chip where 3'-AGAACGT is located. The chip contains cells that include multiple copies of a particular probe. Thus, the image file will contain fluorescence intensities, one for each probe (or cell). By analyzing the fluorescence intensities associated with a specific probe, it becomes possible to extract sequence information from such arrays using the methods of the invention disclosed herein.

For ease of reference, one may call bases by assigning the bases the following codes:

| Code | Group | Meaning |
| --- | --- | --- |
| A | A | Adenine |
| C | C | Cytosine |
| G | G | Guanine |
| T | T(U) | Thymine (Uracil) |
| M | A or C | aMino |
| R | A or G | puRine |
| W | A or T(U) | Weak interaction (2 H bonds) |
| Y | C or T(U) | pYrimidine |
| S | C or G | Strong interaction (3 H bonds) |
| K | G or T(U) | Keto |
| V | A, C or G | not T(U) |
| H | A, C or T(U) | not G |
| D | A, G or T(U) | not C |
| B | C, G or T(U) | not A |
| N | A, C, G, or T(U) | Insufficient intensity to call |
| X | A, C, G, or T(U) | Insufficient discrimination to call |

Most of the codes conform to the IUPAC standard. However, code N has been redefined and code X has been added.

Sequencing Utilizing Mismatch Information

The present invention provides methods of sequencing nucleic acid sequences utilizing mismatch information.

When used herein, "mismatch information" relates to base mismatches between or among nucleic acid probes. Mismatch information may include the number of base mismatches, the location of the base mismatches and the base differences. The mismatch information may be combined with information from the hybridization intensity to sequence the nucleic acid sequence with a high degree of accuracy. In a preferred embodiment, the present invention is utilized for de novo sequencing of nucleic acids.

In order to illustrate what mismatch information or the pattern of mismatches may include, a hypothetical example will be described. Suppose the target nucleic acid is an 8-mer (meaning that the target nucleic acid consists of eight bases or nucleotides) and that the target is exposed to a chip including the complete set of 8-mer probes. In order to simplify this example, further assume that the 1 probe that is perfectly complementary to the target and the 24 probes that contain a single base mismatch (i.e., perfectly complementary except for a single base mismatch) have the highest hybridization intensities because they hybridize most strongly to the target.

Thus, if the target is ACTGGTCT-3', the following would be the probes having the highest measured intensities in this example:

```
Perfect complement      TGACCAGA-5'
One base mismatches     GGACCAGA-5'
                        AGACCAGA-5'
                        CGACCAGA-5'
                        TAACCAGA-5'
                        TCACCAGA-5'
                        TTACCAGA-5'
                           .
                           .
                           .
``` and so forth for the other six positions. The set of these 25 probes may be analyzed to sequence the target nucleic acid. Although typically, the target nucleic acid is longer than the probes, the example provides a good illustration of aspects of the present invention.

For many reasons, probes that are perfectly or exactly complementary to the target may not have the highest hybridization intensities. Therefore, a probe that is perfectly complementary to the target often cannot be identified from the rank order of hybridization intensities. The present invention utilizes mismatch information among the nucleic acid probes to sequence the target where all of the nucleic acid probes that are perfectly complementary to part of the target may not be readily identified.

The present invention identifies neighbor-rich probes which are then utilized to sequence the target nucleic acid. A "neighbor-rich probe" is a probe that is related to many other probes in the probe space by a single base mismatch. A probe that has a single base mismatch with another probe will be referred to as a "single base mismatch neighbor." Neighbor-rich probes may be identified according to mismatch information as follows.

After a set of probes is identified, each probe in the set is compared to the other probes to determine how the probe's sequence compares to the other probes. In the example above, one probe differs from the other 24 probes by a single base mismatch (i.e., m=1, where m is the number of mismatches). Thus, this one probe is related to or has 24 single base mismatch neighbors.

By contrast, twenty-four probes differ from 3 other probes in the set by a single base mismatch and from 21 other probes in the set by a double base mismatch (i.e., m=2). In this simple example, the perfectly complementary probe may be identified as a neighbor-rich probe from the mismatch information because it has many single mismatch neighbor probes in the probe space. The perfectly complementary probe had 8 times as many single mismatch neighbor probes as nearly-complementary probes. Although the hybridization conditions did not allow identification of the perfectly complementary probes, an analysis of mismatch information may be utilized to identify the perfectly complementary probe. In practice, mismatch information may be utilized for de novo sequencing of a target nucleic acid where oligonucleotide probes are contacted with the target under conditions that do not allow differentiation between those probes that are perfectly complementary to part of the target and those probes that are not.

In this example, the sequence of the target was known. However, in many applications including de novo sequencing the sequence of the target is unknown. Nevertheless, the example is useful in demonstrating how neighbor-rich probes may be identified.

A. One Embodiment

Figure 6:
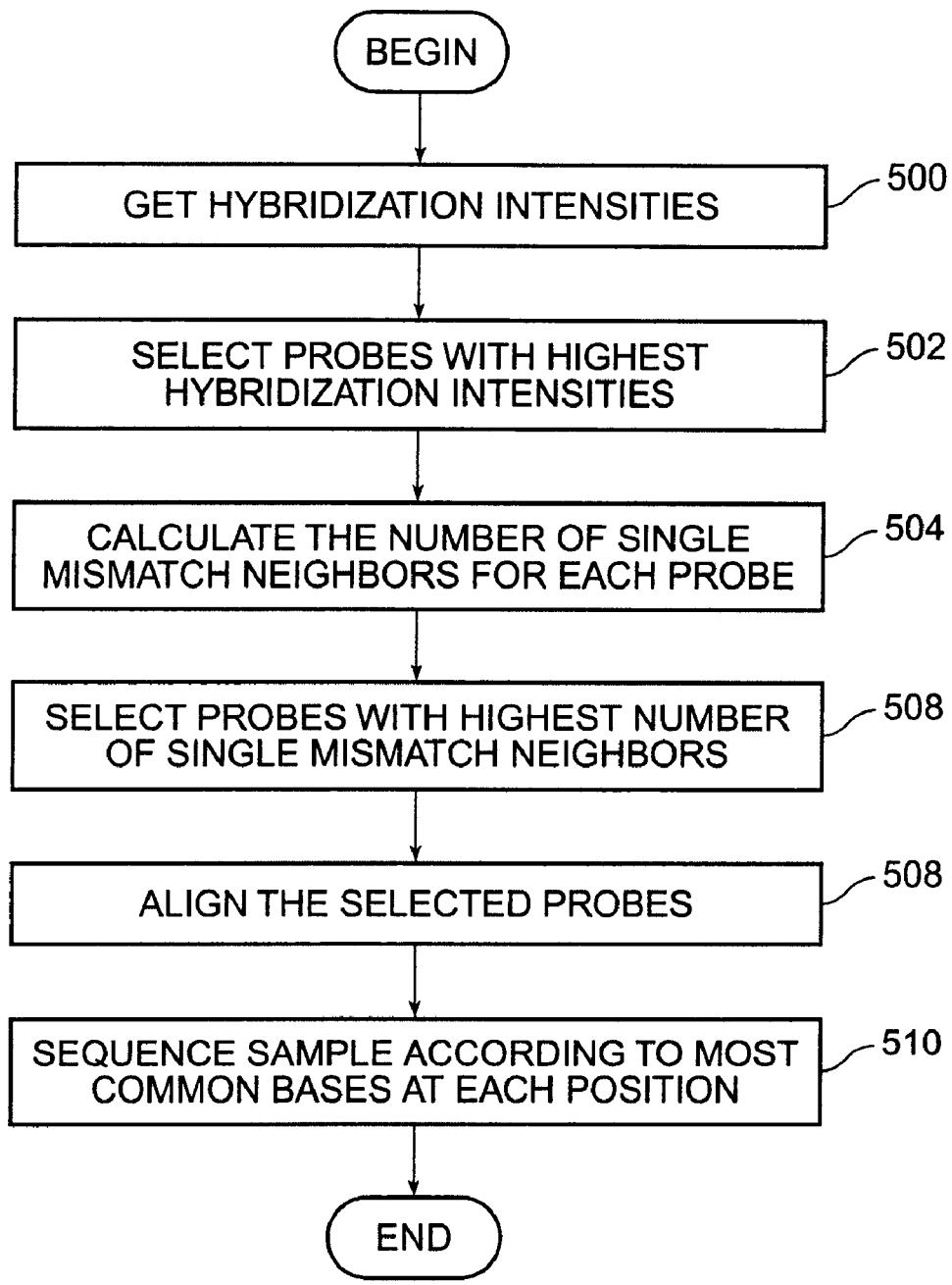
FIG. 6 shows a high level flow of sequencing utilizing mismatch information.

FIG. 6 shows a high level flow of sequencing utilizing mismatch information. At step 500, hybridization intensities from probes or other data indicative of binding affinity are input into the system. The system may receive the hybridization intensities many different ways. The system may operate the scanning device directly, the system may receive the hybridization intensities from another computer system that measured the intensities, or an operator may manually enter the data. There may be thousands or tens of thousands of hybridization intensities that correspond to nucleic acid probes on a chip. Typically, the chip includes all possible probes of a specific length in order to sequence the target.

At step 502, the system selects a set of probes associated with the highest hybridization intensities (i.e., that show the strongest binding affinity). Selecting the probes with the highest hybridization intensities may be done in any number of ways. For example, the system may use an intensity threshold value and select the probes whose hybridization intensities are higher than the intensity threshold (e.g., 100 photon counts). The system may select a specific number or percentage of probes (e.g., 50 probes or the top 10%) that have the highest hybridization intensities. Additionally, the system may select the probes that have a hybridization intensity greater than a specific percentage (e.g., 40%) of the highest hybridization intensity.

After the set of probes with the strongest binding affinity is selected, the system calculates the number of single base mismatch neighbors for each probe in the set at step 504. For example, in one embodiment, a probe is first selected in order to compare the selected probe to the other probes. The system then determines how many of the other probes in the set are identical to the selected probe except for a single base mismatch at one base position. The number of single base mismatch neighbors is calculated for each of the probes having the highest hybridization intensities. Additionally, the system may calculate and utilize the number of double base mismatches in an extension of the concepts herein.

At step 506, the system selects the probes in the set with the highest number of single base mismatch neighbors. Selecting the probes with the highest number of neighbors may be done in any number of ways including utilizing a threshold, a specific number of the probes, or greater than a specific percentage of the highest number of neighbors. In one embodiment, the system selects the probes in the set with the highest number of neighbors and the highest hybridization intensities. In other words, a second intensity threshold is utilized to further reduce the set of probes.

The selected probes with the highest number of single base mismatch neighbors are the neighbor-rich probes. The neighbor-rich probes are then aligned at step 508. The neighbor-rich probes are aligned or compiled so that they have the most bases in common. Thus, neighbor-rich probes that have a single base mismatch are aligned to form an aligned set of probes. Aligned sets of probes are then aligned in an offset fashion in the way that reduces the number of base mismatches between sets of probes. At step 510, the aligned probes are utilized to sequence the target nucleic acid sequence. The target may be sequenced in many different ways including the formation of a consensus sequence may be produced as described in the following example.

B. Example

A target of 5'-AGTTGTAGTGGATGG (SEQ ID NO:1) was exposed to a chip containing 8-mer probes. The highest hybridization intensity was 331 photon counts. An intensity threshold of 90 photon counts was utilized and there were 133 probes that had a hybridization intensity greater than the intensity threshold of 90. These 133 probes provided the set of probes with the highest hybridization intensities and are as follows:

| probe | intensity | m = 1 | m = 2 |
|---|---|---|---|
| 3'-ACATCACC | 331 | 12 | 10 |
| 3'-CATCACCT | 286 | 11 | 12 |
| 3'-ATCACCTA | 323 | 10 | 8 |
| 3'-CATCACCA | 253 | 8 | 12 |
| 3'-ACAACATC | 331 | 7 | 10 |
| 3'-AATCACCT | 131 | 7 | 14 |
| 3'-ACATCACA | 330 | 7 | 10 |
| 3'-ACCTACCA | 280 | 7 | 6 |
| 3'-CACCTACC | 204 | 7 | 2 |
| 3'-ACTCACCT | 188 | 7 | 11 |
| 3'-CCATCACC | 270 | 6 | 13 |
| 3'-TTCACCTA | 134 | 6 | 10 |
| 3'-ACACCACC | 98 | 6 | 14 |
| 3'-TCAACATC | 331 | 6 | 10 |
| 3'-TCATCACC | 238 | 5 | 17 |
| 3'-CTCACCTA | 203 | 5 | 10 |
| 3'-ACACCAAC | 122 | 5 | 10 |
| 3'-ACACCTAC | 272 | 5 | 8 |
| 3'-ACCTACCC | 108 | 5 | 7 |
| 3'-TCATCACA | 147 | 5 | 7 |
| 3'-CAACATCA | 275 | 5 | 5 |
| 3'-CAACACCT | 183 | 5 | 15 |
| 3'-CACCACCT | 113 | 5 | 15 |
| 3'-ATCACCAC | 157 | 5 | 6 |
| 3'-TCCACCTA | 112 | 5 | 7 |
| 3'-TCACCTAC | 248 | 5 | 6 |
| 3'-TGCACCTA | 105 | 5 | 6 |
| 3'-TATCACCT | 143 | 5 | 13 |
| 3'-CCACCTAC | 208 | 5 | 5 |
| 3'-ACAACACC | 147 | 5 | 18 |
| 3'-CCAACATC | 325 | 4 | 10 |
| 3'-GCATCACC | 262 | 4 | 15 |
| 3'-GCACCTAC | 199 | 4 | 6 |
| 3'-AACATCAC | 148 | 4 | 1 |
| 3'-AGTCACCT | 90 | 4 | 9 |
| 3'-CAACATCT | 101 | 4 | 5 |
| 3'-CCATCACA | 181 | 4 | 9 |
| 3'-CGCACCTA | 127 | 4 | 6 |
| 3'-TCAACACC | 129 | 4 | 13 |
| 3'-ATCACCTT | 129 | 4 | 9 |
| 3'-ACACCTAA | 155 | 4 | 6 |
| 3'-CAACACCA | 100 | 4 | 14 |
| 3'-ACACACCT | 305 | 4 | 11 |
| 3'-TCACCTAA | 176 | 4 | 4 |
| 3'-ACACACCA | 174 | 4 | 8 |
| 3'-CAGCACCT | 111 | 4 | 13 |
| 3'-ATCACCAA | 115 | 4 | 11 |
| 3'-ATCACCTC | 137 | 4 | 13 |
| 3'-GCATCACA | 156 | 4 | 7 |
| 3'-TACACCTA | 96 | 4 | 7 |
| 3'-CCTCACCT | 102 | 4 | 14 |
| 3'-TCAACCTC | 132 | 4 | 6 |
| 3'-CACCACCA | 91 | 4 | 13 |
| 3'-CATCACCC | 131 | 4 | 17 |
| 3'-GCAACATC | 319 | 4 | 9 |
| 3'-CATCAACC | 105 | 4 | 6 |
| 3'-CACCTACA | 187 | 4 | 5 |
| 3'-ACACCATC | 128 | 4 | 13 |
| 3'-ACCTACCT | 112 | 4 | 11 |
| 3'-ATTCACCT | 91 | 4 | 10 |
| 3'-CCACCTAA | 111 | 4 | 5 |
| 3'-GCACCTAA | 127 | 4 | 3 |
| 3'-AGCACCTA | 148 | 4 | 11 |
| 3'-GTCACCTA | 141 | 3 | 12 |
| 3'-ACATCACT | 164 | 3 | 13 |
| 3'-CATCACCG | 163 | 3 | 15 |
| 3'-CCCTACCA | 133 | 3 | 6 |
| 3'-ACCTACCG | 119 | 3 | 8 |
| 3'-ACAGCACC | 101 | 3 | 14 |
| 3'-ATCACCCA | 106 | 3 | 12 |
| 3'-CGTCACCT | 114 | 3 | 12 |
| 3'-CAACATCC | 148 | 3 | 7 |
| 3'-ACAACCTC | 114 | 3 | 10 |
| 3'-ATCAACCT | 120 | 3 | 7 |
| 3'-ACCAACCA | 104 | 3 | 12 |
| 3'-GCCTACCA | 111 | 3 | 4 |
| 3'-CACCAACA | 119 | 3 | 8 |
| 3'-ACTCACCA | 143 | 3 | 12 |
| 3'-ACCACCTA | 141 | 3 | 17 |
| 3'-CTATCACC | 100 | 3 | 4 |
| 3'-CAACATCG | 137 | 3 | 4 |
| 3'-ACGCACCT | 110 | 3 | 11 |
| 3'-TCACCATC | 102 | 3 | 10 |
| 3'-CACACCTA | 102 | 3 | 7 |
| 3'-CACCTACT | 106 | 3 | 6 |
| 3'-CACCAACC | 103 | 3 | 11 |
| 3'-ATCACCTG | 106 | 3 | 9 |
| 3'-ACATCACG | 149 | 3 | 13 |
| 3'-GCAACCTC | 93 | 3 | 4 |
| 3'-AAGCACCT | 92 | 3 | 11 |
| 3'-ATCATCAC | 90 | 3 | 6 |
| 3'-TCCTACCA | 91 | 3 | 4 |
| 3'-ATCAACCA | 103 | 3 | 5 |
| 3'-ACCAACCT | 97 | 3 | 10 |
| 3'-GATCACCT | 102 | 3 | 14 |
| 3'-TCACCAAC | 102 | 3 | 10 |
| 3'-ACCTACTC | 102 | 3 | 3 |
| 3'-CACCTACG | 99 | 3 | 5 |
| 3'-CCTCACCA | 91 | 3 | 12 |
| 3'-ATCACCAT | 125 | 3 | 8 |
| 3'-TCAACCTA | 104 | 2 | 8 |
| 3'-ACCATCAC | 113 | 2 | 5 |
| 3'-CATCTACC | 94 | 2 | 8 |
| 3'-CAATCACC | 94 | 2 | 6 |
| 3'-ACATCAAC | 154 | 2 | 15 |
| 3'-ACCTACAC | 113 | 2 | 5 |
| 3'-ACACATCA | 128 | 2 | 6 |
| 3'-CCACATCA | 90 | 2 | 7 |
| 3'-TATCACCA | 97 | 2 | 12 |
| 3'-CACATCAC | 154 | 2 | 3 |
| 3'-TCAACACA | 97 | 2 | 8 |
| 3'-TACCACCT | 91 | 2 | 9 |
| 3'-ATCCACCT | 105 | 2 | 11 |
| 3'-ACACACCG | 122 | 2 | 5 |
| 3'-ACACCACA | 90 | 2 | 14 |
| 3'-ATATCACC | 96 | 2 | 12 |
| 3'-TACATCAC | 128 | 2 | 2 |
| 3'-CAACCTAC | 116 | 1 | 6 |
| 3'-CATCACAA | 107 | 1 | 7 |
| 3'-ACCTCACC | 102 | 1 | 13 |
| 3'-ACCAACTC | 96 | 1 | 9 |
| 3'-TATCAACC | 94 | 1 | 6 |
| 3'-TACCTACC | 99 | 1 | 8 |
| 3'-ACCACATC | 128 | 1 | 12 |
| 3'-ATCACAAC | 153 | 1 | 5 |
| 3'-CCTACATC | 93 | 1 | 4 |

-continued

| probe | intensity | m = 1 | m = 2 |
|---|---|---|---|
| 3'-CACCTAAC | 95 | 1 | 7 |
| 3'-CCTACCAA | 128 | 0 | 0 |
| 3'-TACACACC | 91 | 0 | 2 |
| 3'-CAACCATC | 93 | 0 | 5 |
| 3'-GTTAAGAG | 329 | 0 | 0 |
| 3'-AGCAACAT | 94 | 0 | 3 |
| 3'-TCTATGCG | 33 | 0 | 0 | where the columns denoted m=1 and m=2 indicate the number of single and double base mismatch neighbors, respectively. Thus, each probe was compared to the other 132 probes to determine the number of single and double base mismatches the probe had with the other probes. The highest number of single base mismatch neighbor probes was 12 and the probes are presented in decreasing order according to the number of single base mismatch neighbor probes.

A set of neighbor-rich probes was identified by selecting the probes that had a hybridization intensity greater than 40% of 331 (0.40*331=132.4), and the number of single base mismatch neighbors greater than 40% of 12 (0.40*12 =4.8). The following is the list of neighbor-rich probes selected in this manner:

| probe | intensity | m = 1 | m = 2 |
|---|---|---|---|
| 3'-ACACCTAC | 272 | 5 | 8 |
| 3'-ACATCACC | 331 | 12 | 10 |
| 3'-ACATCACA | 330 | 7 | 10 |
| 3'-ACAACACC | 147 | 5 | 18 |
| 3'-ACAACATC | 331 | 7 | 10 |
| 3'-ACCTACCA | 280 | 7 | 6 |
| 3'-ATCACCAC | 157 | 5 | 6 |
| 3'-ATCACCTA | 323 | 10 | 8 |
| 3'-ACTCACCT | 188 | 7 | 11 |
| 3'-CAACATCA | 275 | 5 | 5 |
| 3'-CAACACCT | 183 | 5 | 15 |
| 3'-CCACCTAC | 208 | 5 | 5 |
| 3'-CCATCACC | 270 | 6 | 13 |
| 3'-CTCACCTA | 203 | 5 | 10 |
| 3'-CATCACCT | 286 | 11 | 12 |
| 3'-CATCACCA | 253 | 8 | 12 |
| 3'-TCACCTAC | 248 | 5 | 6 |
| 3'-TCATCACC | 238 | 5 | 17 |
| 3'-TCATCACA | 147 | 5 | 7 |
| 3'-TCAACATC | 331 | 6 | 10 |
| 3'-TTCACCTA | 134 | 6 | 10 |
| 3'-TATCACCT | 143 | 5 | 13 | where again m=1 and m=2 indicates the number of single and double base mismatch neighbors, respectively, with other probes in the set of probes with a hybridization intensity greater than 90.

Once the neighbor-rich probes having a high hybridization intensity and high number of single base mismatch neighbors have been selected, the neighbor-rich probes were utilized to sequence the target nucleic acid sequence. The system utilized the frequency of bases at each position to produce a consensus sequence, where a "consensus sequence" is a sequence generated by neighbor-rich probes to sequence the target.

In order to produce a consensus sequence, the system aligned the neighbor-rich probes so that each probe had the highest number of bases in common with other probes. The following are the aligned neighbor-rich probes with the complement of the target sequence shown for reference. The target sequence is known in this example but the target sequence may be an unknown sequence or only partially known.

```
                                          (SEQ ID NO:2)
                       A C A C C T A C
                       A C A T C A C C
                       A C A T C A C A
                 A C A A C A C C
                 A C A A C A T C
                         A C C T A C C A
                           A T C A C C A C
                           A T C A C C T A
                           A C T C A C C T
                 C A A C A T C A
                         C A A C A C C T
                         C C A C C T A C
                 C C A T C A C C
                           C T C A C C T A
                         C A T C A C C T
                         C A T C A C C A
                             T C A C C T A C
                 T C A T C A C C
                       T C A T C C A
           T C A A C A T C
                             T T C A C C T A
                             T A T C A C C T
Target     T C A A C A T C A C C T A C C
complement-
```

After the neighbor-rich probes are aligned, the system counts the number or frequency of each base (A, C, G and T) at each position. After the frequency of bases at each position is calculated, the system produces a consensus sequence. In one embodiment, the base that occurred the most at a position is utilized to produce the consensus sequence if the base occurred more than 2 times and the frequency that the base occurred is greater than 50% at that position. The following is a matrix of base vs. frequency that was used to produce the consensus sequence in this manner:

```
              Frequency
                                                 (SEQ ID NO:3)
Base      A 2 0 5 8  2 17  2  0 17  2  2 3 5 0 0
          C 0 5 0 1 15  4  3 22  2 16 16 1 1 2 1
          G 0 0 0 0  0  0  0  0  0  0  0 0 0 0 0
          T 1 0 0 2  1  1 18  1  1  1  0 9 0 0 0
Consensus   — C A A  C  A  T  C  A  C  C T A — —
```

Therefore, for the first position in the consensus sequence (left-most in the matrix), base A occurred 66% (2 divided by 3) of the time which is greater than 50%, however, the base did not occur more than 2 times so the base is called as ambiguous (i.e., "-").

The consensus sequence is the complement of the target; thus, the target is sequenced according to the complement of the consensus sequence. In this example, the target sequence was 5'-AGTTGTAGTGGATGG (SEQ ID NO:1) and it was correctly sequenced as 5'-GTTGTAGTGGAT (SEQ ID NO:4, the terminal bases being ambiguous). The parameters for producing the consensus sequence may be varied according to the experimental data. For example, if the consensus sequence was formed solely by the bases that occur most often at each position, the consensus sequence would be perfectly complementary to the target nucleic acid for this data. However, this will not always be the case.

Software Appendix A provides a BASIC source code illustration of this embodiment of the invention. The source code is written in Quick BASIC for an IBM compatible personal computer.

C. Alternate Embodiment

Figure 7:
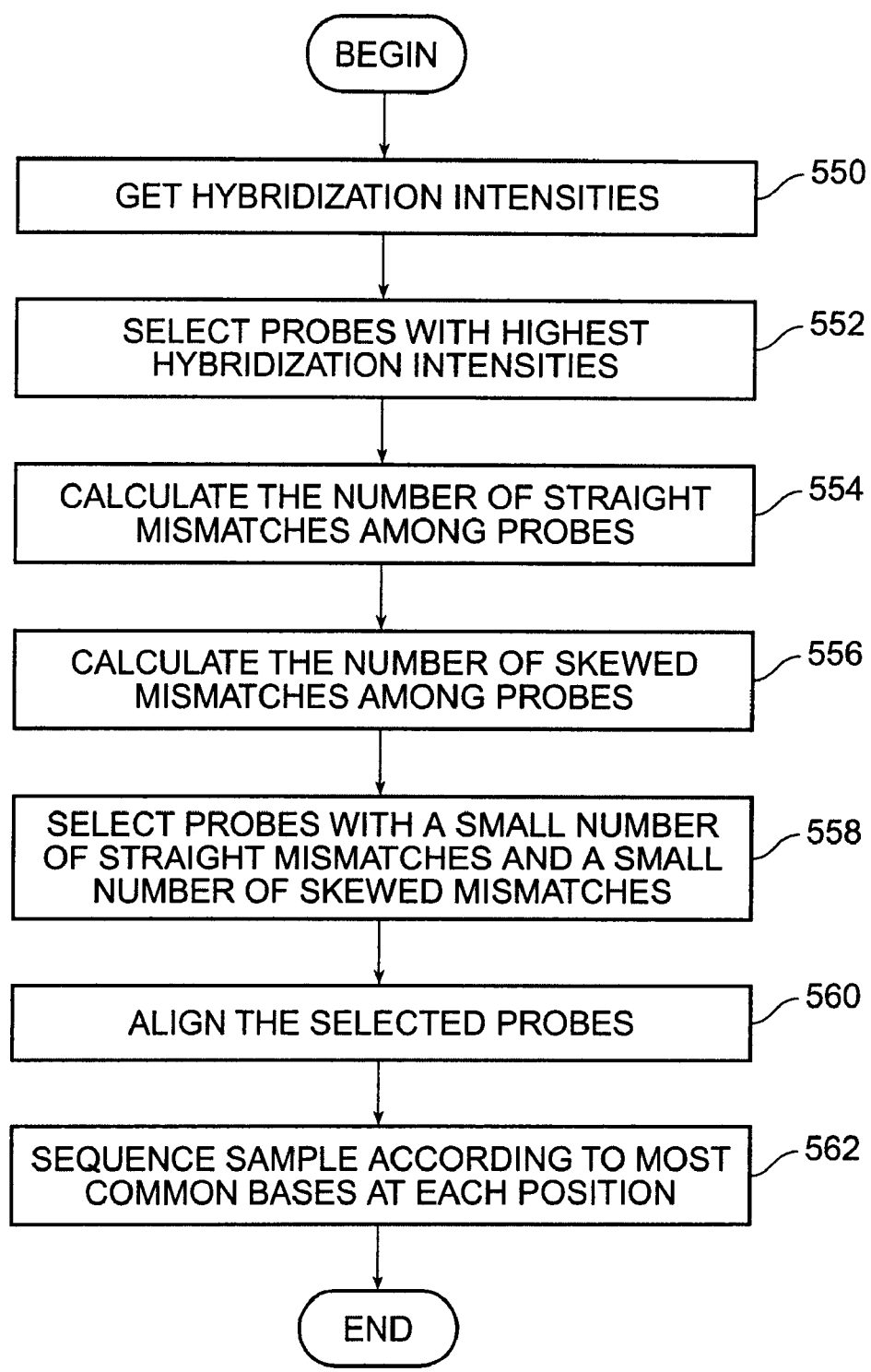
FIG. 7 shows a high level flow of another embodiment of sequencing utilizing mismatch information.

FIG. 7 shows a high level flow of another embodiment of sequencing utilizing mismatch information. At step 550, hybridization intensities are input into the system. The system may receive the hybridization intensities many different ways. The system may operate the scanning device directly, the system may receive the hybridization intensities from another computer system that measured the intensities, or an operator may manually enter the data.

At step 552, the system selects a set of probes associated with the highest hybridization intensities. Selecting the probes with the highest hybridization intensities may be done in any number of ways. For example, the system may use an intensity threshold value and select the probes whose hybridization intensities are higher than the intensity threshold. The system may select a specific number or percentage of probes that have the highest hybridization intensities. Alternatively, the system may select the probes that have a hybridization greater than a specific percentage of the highest hybridization intensity.

After the set of probes with the highest hybridization intensities is selected, the system calculates the number of straight mismatches for each probe in the set at step 554. "Straight mismatches" refers to base mismatches between probes where the bases at corresponding positions are compared (e.g., as was done in the previous embodiment). For example, a probe 3'-AACAT is compared to a probe 3'-AACTT by aligning the probes as follows:

```
3'-AACAT
3'-AACTT
```

Each probe has n bases, where n=5. If the base at the 3' end is at position 1, there is a single mismatch at the fourth position where the A and T do not match. Thus, straight mismatches are determined by comparing bases at the same position in each probe (i.e., z=0, where z indicates the number of bases one of the probes was offset from the other probe before comparing).

Figure 8:
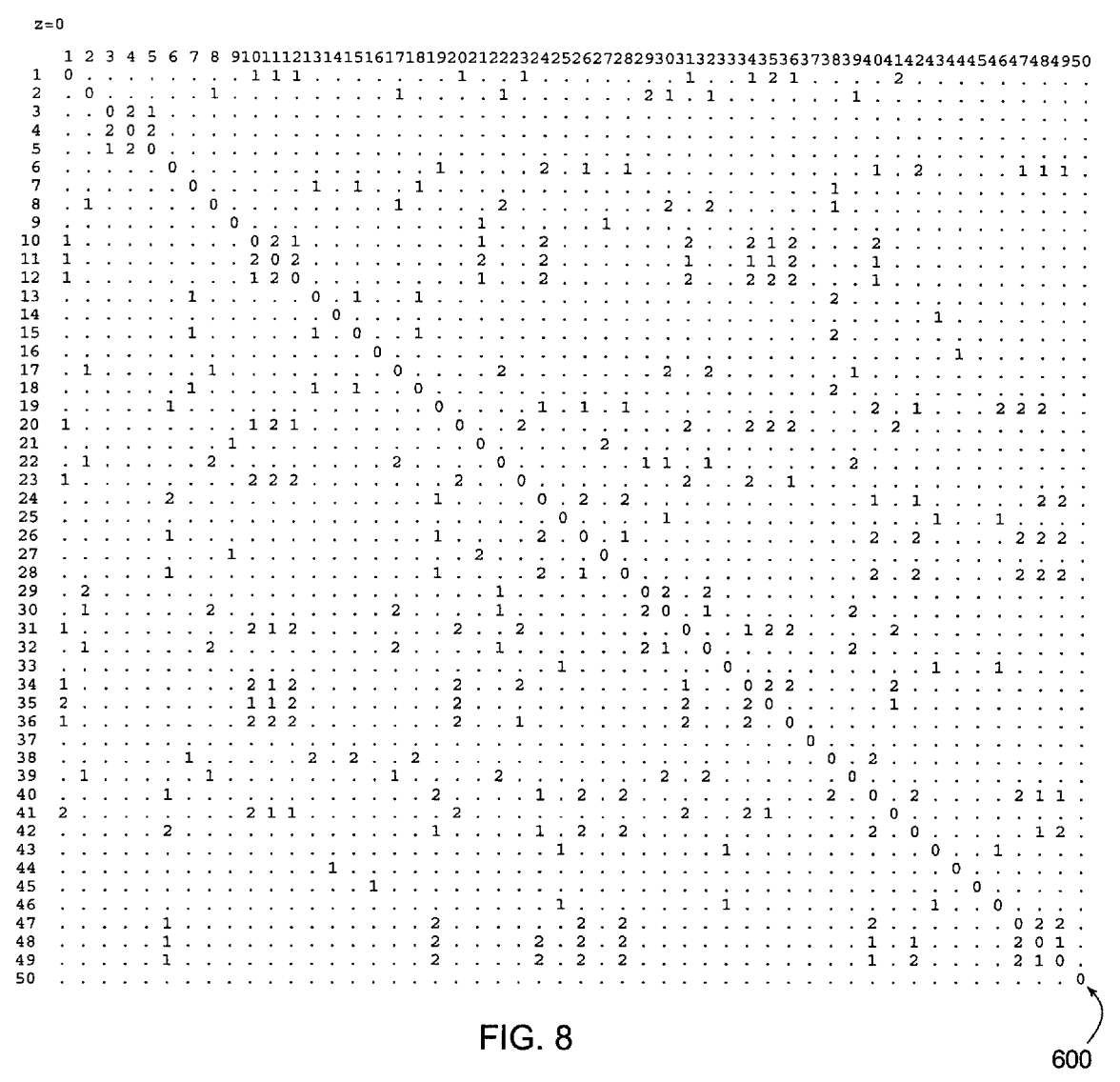

In one embodiment, a matrix is formed to show the straight mismatches between probes. FIG. 8 shows a straight mismatch matrix for 50 probes. For simplicity, each probe is assigned an identification number from 1 to 50. The numbers on the rows and columns of the matrix correspond to the identification number of the probe. The value in the matrix represents the number of straight mismatches between the probes designated by the row and column. If there are more than 2 mismatches, the matrix shows a "." at the appropriate matrix location. Since a diagonal 600 of the matrix shows the number of straight mismatches between the same probe, the diagonal contains 0's because the probe is being compared to itself (i.e., there are no straight mismatches). Also, the matrix is identical on each side of diagonal 600.

The system calculates the number of offset mismatches for each probe in the set at step 556. "Offset mismatches" refers to base mismatches between probes where bases at offset positions are compared. For example, a probe 3'-CGAATCAA is compared to a probe 3'-GCATCAAC by aligning the probes as follows:

```
3'-CGAATCAA
3'-GCATCCAC
```

Each probe has n bases, where n=8. If the base at the 3' end is at position 1, bases at position 1 through 7 (or n−1) of the first probe is compared to bases at position 2 through 8 (or n). As shown, there are two mismatches (double mismatch) when the probes are offset a single base position (i.e., z=1, where z indicates the number of bases one of the probes is offset from the other probe before comparing).

Figure 9:
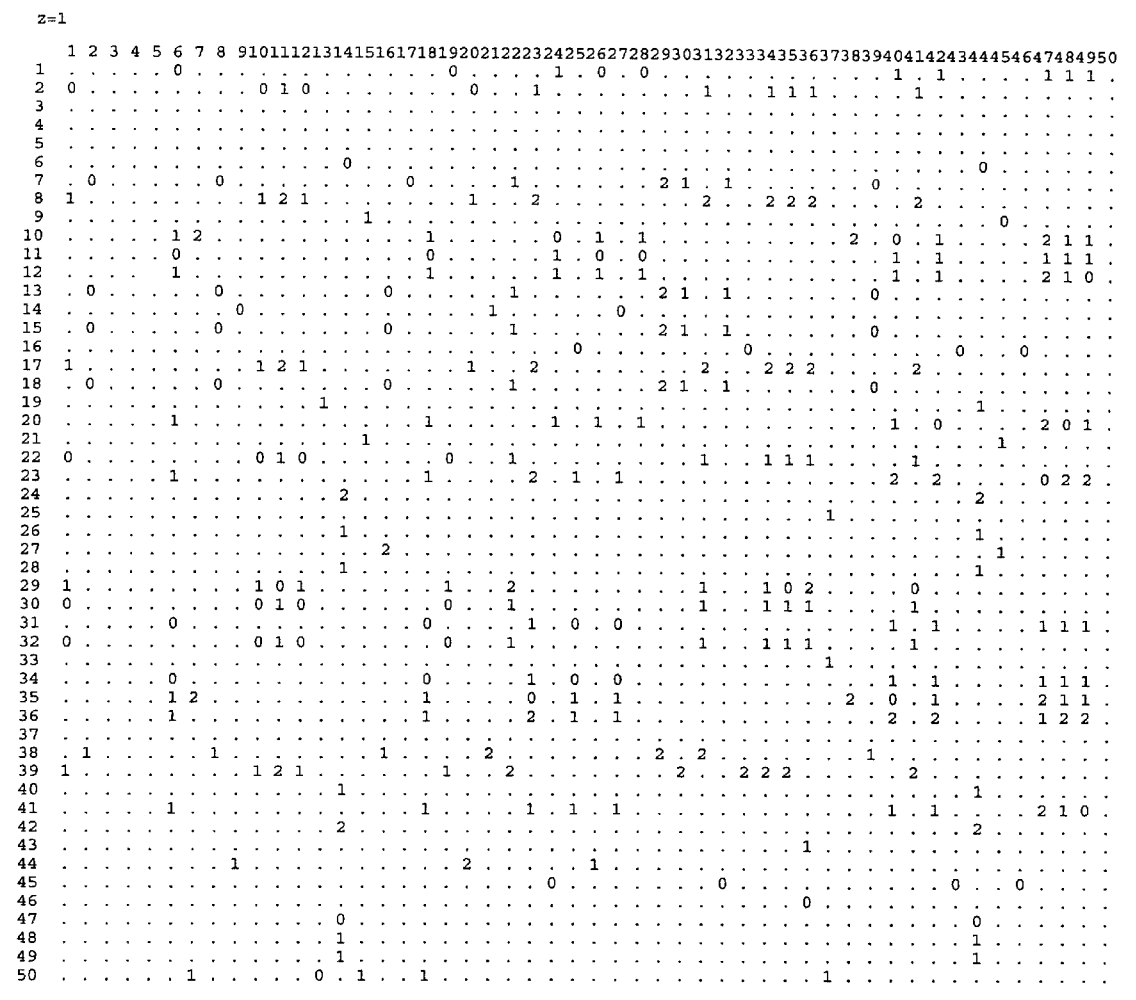

In one embodiment, a matrix is formed to show the offset mismatches between probes. FIG. 9 shows an offset mismatch matrix for 50 probes. As in FIG. 8, the rows and columns of the matrix correspond to the identification number of the probe, which is 1 to 50. The value in the matrix represents the number of offset mismatches between the probes designated by the row and column. If there are more than 2 mismatches, the matrix shows a "." at the appropriate matrix location. As shown, a diagonal will not contain 0's and the matrix is not identical on each side of the diagonal. Although the probes were offset a single base position, the probes may be offset more positions when they are compared in an extension of the principles herein.

At step 558, the system selects the probes with less than some small number straight mismatches and less than some small number of offset mismatches. In one embodiment, the system identifies the probes in the matrices that have less than 2 straight mismatches and less than 3 offset mismatches. The parameters for selecting these probes with few mismatches may be varied according to the experimental data.

The selected probes are then aligned at step 560. The probes are aligned so that they have the most bases in common. The mismatch information concerning the straight mismatches and offset mismatches is utilized to align the probes so that the number of mismatches between the probes is reduced. At step 562, the aligned probes are utilized to sequence the target nucleic acid sequence. The target may be sequenced in many different ways. For example, a consensus sequence may be produced as described in the following example.

D. Example

A target of 5'-AGTTGTAGTGGATGGT (SEQ ID NO:5) was exposed to a chip containing 10-mer probes. Fifty probes were selected that have the highest hybridization intensities (step 552). FIGS. 11 and 12 show the straight and offset mismatch matrices for the fifty probes (steps 554 and 556). Forty-seven probes were selected that have less than 2 straight mismatches with at least one other probe and less than 3 offset mismatches with at least one other probe (step 558).

The straight and offset mismatch information was utilized to align the 47 probes (step 560). For example, FIG. 9 shows that the probe identified as 2 on the row had 0 offset mismatches with the probe identified as 1 on the column.

Therefore, probes 2 and 1 align well if they are offset a single base position. The following are the aligned 47 probes:

```
       AACATCACCT           (SEQ ID NO: 8)
       CAACATCACC           (SEQ ID NO: 9)
        ACATCACCTA          (SEQ ID NO: 10)
      ACAACATCAC            (SEQ ID NO: 11)
       CAACATCACA           (SEQ ID NO: 12)
          ATCACCTACC        (SEQ ID NO: 13)
       AACATCACCA           (SEQ ID NO: 14)
        CACATCACCT          (SEQ ID NO: 15)
```

-continued

| | |
|---|---|
| AACATCACCG | (SEQ ID NO: 16) |
| TCAACATCAC | (SEQ ID NO: 17) |
| CATCACCTAC | (SEQ ID NO: 18) |
| CCAACATCAC | (SEQ ID NO: 19) |
| ACACCTACCA | (SEQ ID NO: 20) |
| CAACATCACG | (SEQ ID NO: 21) |
| GCAACATCAC | (SEQ ID NO: 22) |
| ACATCACCTT | (SEQ ID NO: 23) |
| AACATCACCC | (SEQ ID NO: 24) |
| AGCACCTACC | (SEQ ID NO: 25) |
| AAACATCACC | (SEQ ID NO: 26) |
| ACCATCACCT | (SEQ ID NO: 27) |
| ACATCACCAT | (SEQ ID NO: 28) |
| CACCTACCAA | (SEQ ID NO: 29) |
| ACATCACCTC | (SEQ ID NO: 30) |
| ATCACCTACA | (SEQ ID NO: 31) |
| ACATCACCTG | (SEQ ID NO: 32) |
| ACACATCACC | (SEQ ID NO: 33) |
| GAACATCACC | (SEQ ID NO: 34) |
| TACATCACCT | (SEQ ID NO: 35) |
| TAACATCACC | (SEQ ID NO: 36) |
| CACCTACCAG | (SEQ ID NO: 37) |
| GACATCACCT | (SEQ ID NO: 38) |
| CACATCACCA | (SEQ ID NO: 39) |
| ATCATCACCT | (SEQ ID NO: 40) |
| ACCTACCATC | (SEQ ID NO: 41) |
| ACAACATCAA | (SEQ ID NO: 42) |
| CAACATCACT | (SEQ ID NO: 43) |
| ACATCACCAA | (SEQ ID NO: 44) |
| CACATCACCG | (SEQ ID NO: 45) |
| ACATCACCCT | (SEQ ID NO: 46) |
| CACCTACCAC | (SEQ ID NO: 47) |
| CATCACCTAA | (SEQ ID NO: 48) |
| TCACCTACCA | (SEQ ID NO: 49) |
| CACCTACCAT | (SEQ ID NO: 50) |
| CCATCACCTA | (SEQ ID NO: 51) |
| ACATCACCCA | (SEQ ID NO: 52) |
| ACATCACCGA | (SEQ ID NO: 53) |
| ATCAACATCA | (SEQ ID NO: 54) |

After the selected probes were aligned, the system counts the number of occurrences of each base (A, C, G and T) at each position. After the frequency of bases at each position is calculated, the system produces a consensus sequence which should be complementary to the target sequence. If the system utilized bases that occurred more than 2 times and the frequency that the base occurred is greater than 50% at that position, the consensus sequence 3'-CAACATCACCTACCA (SEQ ID NO:6) is produced.

The consensus sequence is ideally the complement of the target; thus, the target is sequenced according to the complement of the consensus sequence (consensus' where the prime denotes the complement). In this example, the target and consensus' sequence were as follows:

| | |
|---|---|
| Target | AGTTGTAGTGGATGGT |
| Consensus' | GTTGTAGTGGATGGT |

(SEQ ID NO:5 and SEQ ID NO:7, one terminal base of the consensus sequence being ambiguous). Thus, the target was sequenced with a high degree of accuracy utilizing mismatch information. The parameters for producing the consensus sequence may be varied according to the experimental data.

Software Appendix B provides a BASIC source code illustration of this embodiment of the invention. The source code is written in Quick BASIC for an IBM compatible personal computer.

Conclusion

The above description is illustrative and not restrictive. Many variations of the invention will become apparent to those of skill in the art upon review of this disclosure. Merely by way of example, while the invention is illustrated with particular reference to the evaluation of DNA (natural or unnatural), the methods can be used in the analysis from chips with other materials synthesized thereon, such as RNA. The scope of the invention should, therefore, be determined not with reference to the above description, but instead should be determined with reference to the appended claims along with their full scope of equivalents.

```
'SEARCH.BAS 11/21/94
'Finds pixels with intensities greater than fmin
'Calculates the match score of bright pixels
'The input file eightmer.dat is based on fs8mer.exe
'The output file score.dat lists the bright pixels
'  and gives the number of 1 and 2 mismatch-related
'  pixels
DIM a$(1000), f%(1000), m1%(1000), m2%(1000)
tstart = TIMER
inf$ = "eightmer.dat"
outf$ = "score.dat"
OPEN inf$ FOR INPUT AS #1
OPEN outf$ FOR OUTPUT AS #2
CLS
'Read the input file and store the bright pixels
fmin = 90 'threshold value for inclusion
n = 0: fmax = 0
WHILE NOT EOF(1)
LINE INPUT #1, g$
seq$ = MID$(g$, 1, 8)
intens = VAL(MID$(g$, 9, 6))
IF intens >= 90 THEN
    n = n + 1
    a$(n) = seq$
    f%(n) = intens
    IF intens > fmax THEN fmax = intens
    PRINT n;
END IF
WEND
PRINT
PRINT USING "#### intensity values above ####"; n; fmin
```

```
                                    -continued
PRINT USING "Highest intensity is ####"; fmax
'Calculate m1 and m2 for each bright pixel
'    m1 and m2 are the number of other pixels that are related
'    by 1 and 2 mismatches, respectively
m1max = 0  'Keep track of highest m1 score
FOR j = 1 TO n
PRINT j = 1 TO n
PRINT j;
FOR i = 1 TO n
m = 0
FOR k = 1 TO 8
IF MID$(a$(j), k, 1) <> MID$(a$(i), k, 1) THEN m = m + 1
NEXT k
IF m = 1 THEN m1%(j) = m1%(j) + 1
IF m = 2 THEN m2%(j) = m2%(j) + 1
NEXT i
IF m1%(j) > m1max THEN m1max = m1%(j)
NEXT j
PRINT #2, USING "SEARCH.BAS    &    &"; DATE$; TIME$
PRINT #2, USING "Input file: &      Output file: &"; inf$; outf$
PRINT #2, USING "#### intensity values above ####"; n; fmin
PRINT #2, USING "Highest intensity is ####"; fmax
PRINT #2, USING "Greatest number of 1-mismatch relations is ##";
m1max
PRINT #2,
PRINT #2, "List of probes with highest intensity and best matching"
PRINT #2, "  f     m1   m2     sequence"
FOR k = 1 TO n
IF f%(K) > .4 * fmax AND m1%(K) > .4 * m1 max THEN
        PRINT #2, USING "#### ### ### &"; f%(K); m1%(K);
        M2%(k); a$(k)
END IF
NEXT k
PRINT #2, CHR$(12)
'Sort according to f
s% = n \ 2
DO WHILE s% > 0
        FOR i% = s% TO n - 1
        j% = i% - s% + 1
        FOR j% = (i% - s% + 1) TO 1 STEP -s%
            IF f%(j%) >= f%(j% + s%) THEN EXIT FOR
            SWAP f%(j%), f%(j% + s%)
            SWAP m1%(j%), m1%(j% + s%)
            SWAP m2%(j%), m2%(j% + s%)
            SWAP a$(j%), a$(j% + s%)
        NEXT j%
        NEXT i%
        s% = s% \ 2
LOOP
PRINT #2,
PRINT #2, "  f     m1   m2     sequence"
FOR k = 1 TO n
PRINT #2, USING "#### ### ### &"; f%(k); m1%(k); m2%(k); a$(k)
NEXT k
PRINT CHR$(12)
'Sort according to m1
s% = n \ 2
DO WHILE s% > 0
        FOR i% = s% TO n - 1
        j% = i% - s% + 1
        FOR j% = (i% - (s% + 1) TO 1 STEP -s%
            IF m1%(j%) >= m1%(j% + s%) THEN EXIT FOR
            SWAP f%(j%), f%(j% + s%)
            SWAP m1%(j%), m1%(j% + s%)
            SWAP m2%(j%), m2%(j% + s%)
            SWAP a$(j%), a$(j% + s%)
        NEXT j%
        NEXT i%
        s% = s% \ 2
LOOP
PRINT #2,
PRINT #2, "  f     m1   m2     sequence"
FOR k = 1 TO n
PRINT #2, USING "#### ### ### &"; f%(k); m1%(k); m2%(k); a$(k)
NEXT
PRINT USING "Time= ####.# seconds"; TIMER - tstart
'CONSENS.BAS 1/8/95
'Derive a consensus sequence from the highest scoring probes
DIM a$(70), m%(1, 70, 70), f(70), s(-20 TO 20, 4)
```

```
                                    -continued
CLS
INPUT "Input file; ", inf$
INPUT "Output file: ", outf$
OPEN inf$ FOR INPUT AS #1
OPEN outf$ FOR OUTPUT AS #2
LINE INPUT #1, descr$       'File description
INPUT #1, p1       "Probe length
INPUT #1, n        "Number of sequences
For j = 1 TO n
LINE INPUT #1, a$(j)
NEXT j
CLOSE #1
'Initialize the mismatch matrix
FOR z = 0 TO 1: FOR i = 1 TO n: FOR j = 1 TO n
m%(z, i, j) = 100
NEXT j: NEXT i: NEXT z
PRINT #2,
PRINT #2, "CONSENS.BAS "; DATE$; "  "; TIME$
PRINT #2, : PRINT #2,
PRINT #2, "Input file: "; inf$; "   Output file: "; outf$
PRINT #2, descr$
PRINT #2, USING "The ##   ##-mer sequences with the highest
scores are:";
n; p1
PRINT #2,
FOR j = 1 TO n
PRINT #2, USING "##   &"; j; a$(j)
NEXT j
PRINT #2, : PRINT #2,
z = 0
PRINT #2, USING "z=##"; z
PRINT #2, "       ";
FOR k = 1 TO n: PRINT #2, USING "##"; k; : NEXT k
FOR i = 1 TO n
PRINT #2,
PRINT #2, USING "##   "; i;
FOR j = 1 TO n
        m = 0
        FOR k = 1 TO p1
        IF MID$(a$(j), k, 1) <> MID$(a$(i), k, 1), THEN m = m + 1
        NEXT k
        m%(0, i, j) = m
        IF m <= 2 THEN PRINT #2, USING " #"; m;
        ELSE PRINT #2, " .";
NEXT j
NEXT i
PRINT #2, : PRINT #2,
z = 1
PRINT #2, USING "z=##";
PRINT #2, "       ";
FOR k = 1 TO n: PRINT #2, USING "##"; k; : NEXT k
FOR i = 1 TO n
PRINT #2,
PRINT #2, USING "##   "; i;
FOR j = 1 TO n
        m = 0
        FOR k = 1 TO p1 - 1
        IF MID$(a$(j), k, 1) <> MID$(a$(i), k + 1, 1),
        THEN m = m + 1
        NEXT k
        m%(1, i, j) = m
        IF m <= 2 THEN PRINT #2, USING " #"; m;
        ELSE PRINT #2, " .";
NEXT j
NEXT i
PRINT #2, : PRINT #2,
'Mark all sequences with a 100 tag
FOR i = 1 TO n: f(i) = 100: NEXT i
'Designate the first sequence as the origin
f(1) = 0
'Find the frames of sequences that can be aligned
FOR i = 1 TO n
FOR j = 1 TO n
IF m%(1, i, j) <= 2 AND f(i) <> 100 THEN
        f(j) = f(i) + 1
END IF
NEXT j
NEXT i
FOR i = 1 TO n
```

```
FOR j = 1 TO n
IF m%(1, j, i) <= 2 AND f(i) <> 100 THEN
        f(j) = f(i) - 1
END IF
NEXT j
NEXT i
FOR i = 1 TO n
FOR j = i + 1 TO n
IF m%(0, i, j) <= 1 AND f(i) <> 100 THEN
        f(j) = f(i)
END IF
NEXT j
NEXT i
PRINT #2, : PRINT #2,
PRINT #2, "Alignment criteria: <=1 mismatch allowed for z=0"
PRINT #2, "   <=2 mismatches for z=1"
PRINT #2,
PRINT #2, "The aligned sequences are:"
'Print the aligned sequences
FOR i = 1 TO n
IF f(i) <> 100 THEN
        PRINT #2, SPACE$(15 + f(i)); a$(i)
END IF
NEXT i
PRINT #2, : PRINT #2,
'accumulate the sequence scores
offset = 0
For i = 1 TO n
IF f(i) <> 100 THEN
        FOR k = 1 TO p1
        g = INSTR("ACGT", MID$(a$(i), k, 1))
        s(offset + k + f(i), g) = s(offset + k + f(i), g) + 1
        'PRINT offset + k + f(i); g; "       ";
        NEXT k
END IF
NEXT i
PRINT #2, CHR$(12)
PRINT #2, "CONSENS.BAS "; DATE$; "  "; TIME$
PRINT #2, USING "Input file: &      Output file: &"; inf$; outf$
PRINT #2, USING "### ##mer sequences"; n; p1
PRINT #2, descr$
PRINT #2,
PRINT #2, "The frequencies of bases int he aligned sequences are:"
PRINT #2,
'Print the scores
FOR g = 1 TO 4
FOR j = -10 TO 18
PRINT #2, USING "## "; s(j, g);
'PRINT USING "## "; s(j, g);
NEXT j
PRINT #2,
NEXT g
'Find and print the consensus
c$(0) = "—": c$(1) = "A": c$(2) = "C": c$(3) = "G": c$(4) = "T"
FOR j = -10 TO 18
most = 0; mg = 0: sum = 0: b$ = "—"
FOR g = 1 TO 4
IF s(j, g) > most THEN most = s(j, g): mg = g
sum = sum + s(j, g)
NEXT g
'A base is defined if present in at least 2 sequences
' and 55% of those aligned at that position
IF most >= 3 THEN
        IF most / sum > .5 THEN b$ = c$(mg)
END IF
PRINT #2, USING " & "; b$;
cons$ = cons$ + b$
NEXT j
PRINT #2, : PRINT #2, : PRINT #2, "The consensus sequence
is: "; cons$:
PRINT #2,
PRINT cons$
PRINT #2, : PRINT #2,
PRINT #2, "The correct sequence is TCAACATCACCTACCA"
PRINT #2,
PRINT #2, "The stray sequences are:"
FOR i = 1 TO n
IF f(i) = 100 THEN PRINT #2, SPACE$(5); a$(i)
NEXT i
```

---

What is claimed is:

1. A computer implemented method of sequencing a nucleic acid sequence, the method comprising the steps of:
inputting hybridization intensities into a computer for a plurality of nucleic acid probes, the nucleic acid probes hybridizing with the nucleic acid sequence under conditions that do not allow identification of all nucleic acid probes of the plurality of nucleic acid probes that are perfectly complementary to part of the nucleic acid sequence;
the computer selecting nucleic acid probes from the plurality of nucleic acid probes, wherein the step of selecting nucleic acid probes includes selecting nucleic acid probes with highest numbers of single base mismatch neighbors among the probes, a single base mismatch neighbor being another probe that has the same sequence except for a single base that is different; and
the computer sequencing the nucleic acid sequence according to the selected nucleic acid probes.

2. A computer implemented method of sequencing a nucleic acid sequence, the method comprising the steps of:
inputting hybridization intensities into a computer for a plurality of nucleic acid probes, the nucleic acid probes hybridizing with the nucleic acid sequence under conditions that do not allow identification of all nucleic acid probes of the plurality of nucleic acid probes that are perfectly complementary to part of the nucleic acid sequence;
the computer selecting nucleic acid probes from the plurality of nucleic acid probes, wherein the step of selecting nucleic acid probes includes selecting nucleic acid probes that have fewer than a predetermined number of base mismatches with another probe; and
the computer sequencing the nucleic acid sequence according to the selected nucleic acid probes.

3. A computer implemented method of sequencing a nucleic acid sequence, the method comprising the steps of:
inputting hybridization intensities into a computer for a plurality of nucleic acid probes, the nucleic acid probes hybridizing with the-nucleic acid sequence under conditions that do not allow identification of all nucleic acid probes of the plurality of nucleic acid probes that are perfectly complementary to part of the nucleic acid sequence;
the computer selecting nucleic acid probes from the plurality of nucleic acid probes, wherein the step of selecting nucleic acid probes includes selecting nucleic acid probes with highest hybridization intensities and the nucleic acid probes with the highest hybridization intensities are identified as having hybridization intensities above an intensity threshold; and
the computer sequencing the nucleic acid sequence according to the selected nucleic acid probes.

4. A computer implemented method of sequencing a nucleic acid sequence, the method comprising the steps of:

inputting hybridization intensities into a computer for a plurality of nucleic acid probes, the nucleic acid probes hybridizing with the nucleic acid sequence under conditions that do not allow identification of all nucleic acid probes of the plurality of nucleic acid probes that are perfectly complementary to part of the nucleic acid sequence;

the computer selecting nucleic acid probes from the plurality of nucleic acid probes; and the computer sequencing the nucleic acid sequence according to the selected nucleic acid probes, wherein the sequencing step includes the steps of:

aligning the selected nucleic acid probes so that bases that are common overlap; and sequencing the nucleic acid sequence according to bases that occur most often at each position in the aligned nucleic acid probes.

5. The method of claim 4, wherein the nucleic acid sequence is sequenced as complementary to the bases that occur most often.

6. A computer implemented method of sequencing a nucleic acid sequence, the method comprising the steps of:

inputting hybridization intensities into a computer for a plurality of nucleic acid probes, the nucleic acid probes hybridizing with the nucleic acid sequence;

the computer selecting nucleic acid probes with highest numbers of single base mismatch neighbors among the probes, a single base mismatch neighbor being another probe that has the same sequence except for a single base that is different; and the computer sequencing the nucleic acid sequence according to the selected nucleic acid probes.

7. The method of claim 6, further comprising the step of selecting nucleic acid probes with highest hybridization intensities.

8. The method of claim 7, wherein the nucleic acid probes with the highest hybridization intensities are identified as having hybridization intensities above an intensity threshold.

9. The method of claim 6, wherein the step of selecting includes the step of calculating a number of single base mismatch neighbors for each nucleic acid probe.

10. The method of claim 6, wherein the step of selecting includes the step of comparing double base mismatch neighbors, a double mismatch neighbor being another probe that has the same sequence except for two bases that are different.

11. The method of claim 6, wherein the sequencing step includes the steps of:

aligning the selected nucleic acid probes so that bases that are common overlap; and sequencing the nucleic acid sequence according to bases that occur most often at each position in the aligned nucleic acid probes.

12. The method of claim 11, wherein the nucleic acid sequence is sequenced as complementary to the bases that occur most often.

13. A computer program product that sequences a nucleic acid sequence, comprising:

code that receives as input hybridization intensities for a plurality of nucleic acid probes, the nucleic acid probes hybridizing with the nucleic acid sequence;

code that selects nucleic acid probes with highest numbers of single base mismatch neighbors among the probes, a single base mismatch neighbor being another probe that has the same sequence except for a single base that is different;

code that sequences the nucleic acid sequence according to the selected nucleic acid probes; and a computer readable storage medium that stores the codes.

14. The computer program product of claim 13, wherein the computer readable storage medium is a floppy drive, hard drive, CD-ROM, memory, system memory, memory cache, flash memory, or tape.

15. The computer program product of claim 13, further comprising code that selects nucleic acid probes with highest hybridization intensities.

16. The computer program product of claim 15, wherein the nucleic acid probes with the highest hybridization intensities are identified as having hybridization intensities above an intensity threshold.

17. The computer program product of claim 13, wherein the code that selects includes code that calculates a number of single base mismatch neighbor for each nucleic acid probe.

18. The computer program product of claim 13, wherein the code that selects includes code that compares double base mismatch neighbors, a double mismatch neighbor being another probe that has the same sequence except for two bases that are different.

19. The computer program product of claim 13, wherein the code that sequences includes:

code that aligns the selected nucleic acid probes so that bases that are common overlap; and code that sequences the nucleic acid sequence according to bases that occur most often at each position in the aligned nucleic acid probes.

20. The computer program product of claim 19, wherein the nucleic acid sequence is sequenced as complementary to the bases that occur most often.

21. A computer implemented method of sequencing a nucleic acid sequence, the method comprising the steps of:

inputting hybridization intensities into a computer for a plurality of nucleic acid probes, the nucleic acid probes hybridizing with the nucleic acid sequence;

the computer selecting nucleic acid probes that have fewer than a predetermined number of base mismatches with another probe; and the computer sequencing the nucleic acid sequence according to the selected nucleic acid probes.

22. The method of claim 21, further comprising the step of selecting nucleic acid probes with highest hybridization intensities.

23. The method of claim 22, wherein the nucleic acid probes with the highest hybridization intensities are identified as having hybridization intensities above an intensity threshold.

24. The method of claim 21, wherein each nucleic acid probe includes n bases.

25. The method of claim 24, further comprising the steps of:

comparing bases at positions 1 through n of a first nucleic acid probe to bases at positions 1 through n of a second nucleic acid probe; and counting base mismatches between the first and second nucleic acid probe.

26. The method of claim 24, further comprising the steps of:

comparing bases at positions 1 through n−1 of a first nucleic acid probe to bases at positions 2 through n of a second nucleic acid probe; and counting base mismatches between the first and second nucleic acid probe.

27. The method of claim 21, wherein the sequencing step includes the steps of:

aligning the selected nucleic acid probes so that bases that are common overlap; and sequencing the nucleic acid sequence according to bases that occur most often at each position in the aligned nucleic acid probes.

28. The method of claim 27, wherein the nucleic acid sequence is sequenced as complementary to the bases that occur most often.

29. A computer program product that sequences a nucleic acid sequence, comprising:
- code that receives as input hybridization intensities for a plurality of nucleic acid probes, the nucleic acid probes hybridizing with the nucleic acid sequence;
- code that selects nucleic acid probes that have fewer than a predetermined number of base mismatches with another probe;
- code that sequences the nucleic acid sequence according to the selected nucleic acid probes; and
- a computer readable storage medium that stores the codes.

30. The computer program product of claim 29, wherein the computer readable storage medium is a floppy drive, hard drive, CD-ROM, memory, system memory memory cache, flash memory, or tape.

31. The computer program product of claim 29, further comprising code that selects nucleic acid probes with highest hybridization intensities.

32. The computer program product of claim 31, wherein the nucleic acid probes with the highest hybridization intensities are identified as having hybridization intensities above an intensity threshold.

33. The computer program product of claim 29, wherein each nucleic acid probe includes n bases.

34. The computer program product of claim 33, further comprising:
- code that compares bases at positions 1 through n of a first nucleic acid probe to bases at positions 1 through n of a second nucleic acid probe; and
- code that counts base mismatches between the first and second nucleic acid probe.

35. The computer program product of claim 33, further comprising:
- code that compares bases at positions 1 through n–1 of a first nucleic acid probe to bases at positions 2 through n of a second nucleic acid probe; and
- code that counts base mismatches between the first and second nucleic acid probe.

36. The computer program product of claim 29, wherein the code that sequences includes:
- code that aligns the selected nucleic acid probes so that bases that are common overlap; and
- code that sequences the nucleic acid sequence according to bases that occur most often at each position in the aligned nucleic acid probes.

37. The computer program product of claim 36, wherein the nucleic acid sequence is sequenced as complementary to the bases that occur most often.

38. A computer program product that sequences a nucleic acid sequence, comprising:
- code that receives as input hybridization intensities for a plurality of nucleic acid probes, the nucleic acid probes hybridizing with the nucleic acid sequence under conditions that do not allow identification of all nucleic acid probes of the plurality of nucleic acid probes that are perfectly complementary to part of the nucleic acid sequence;
- code that selects nucleic acid probes from the plurality of nucleic acid probes, wherein the code that selects nucleic acid probes includes code that selects nucleic acid probes with highest numbers of single base mismatch neighbors among the probes, a single base mismatch neighbor being another probe that has the same sequence except for a single base that is different;
- code that sequences and nucleic acid sequence according to the selected nucleic acid probes; and
- a computer readable storage medium that stores the codes.

39. A computer program product that sequences a nucleic acid sequence, comprising:
- code that receives as input hybridization intensities for a plurality of nucleic acid probes, the nucleic acid probes hybridizing with the nucleic acid sequence under conditions that do not allow identification of all nucleic acid probes of the plurality of nucleic acid probes that are perfectly complementary to part of the nucleic acid sequence;
- code that selects nucleic acid probes from the plurality of nucleic acid probes, wherein the code that selects nucleic acid probes includes code that selects nucleic acid probes that have fewer than a predetermined number of base mismatches with another probe;
- code that sequences and nucleic acid sequence according to the selected nucleic acid probes; and
- a computer readable storage medium that stores the codes.

40. A computer program product that sequences a nucleic acid sequence, comprising:
- code that receives as input hybridization intensities for a plurality of nucleic acid probes, the nucleic acid probes hybridizing with the nucleic acid sequence under conditions that do not allow identification of all nucleic acid probes of the plurality of nucleic acid probes that are perfectly complementary to part of the nucleic acid sequence;
- code that selects nucleic acid probes from the plurality of nucleic acid probes, wherein the code that selects nucleic acid probes includes code that selects nucleic acid probes with highest hybridization intensities and the nucleic acid probes with the highest hybridization intensities are identified as having hybridization intensities above an intensity threshold;
- code that sequences and nucleic acid sequence according to the selected nucleic acid probes; and
- a computer readable storage medium that stores the codes.

41. A computer program product that sequences a nucleic acid sequence, comprising:
- code that receives as input hybridization intensities for a plurality of nucleic acid probes, the nucleic acid probes hybridizing with the nucleic acid sequence under conditions that do not allow identification of all nucleic acid probes of the plurality of nucleic acid probes that are perfectly complementary to part of the nucleic acid sequence;
- code that selects nucleic acid probes from the plurality of nucleic acid probes;
- code that sequences and nucleic acid sequence according to the selected nucleic acid probes, wherein the code that sequences includes:
  - code that aligns the selected nucleic acid probes so that bases that are common overlap; and
  - code that sequences the nucleic acid sequence according to bases that occur most often at each position in the aligned nucleic acid probes; and
- a computer readable storage medium that stores the codes.

42. The computer program product of claim 41, wherein the nucleic acid sequence is sequenced as complementary to the bases that occur most often.

* * * * *

UNITED STATES PATENT AND TRADEMARK OFFICE
CERTIFICATE OF CORRECTION

PATENT NO.     : 6,361,937 B1
DATED          : March 26, 2002
INVENTOR(S)    : Stryer, Lubert It is certified that error appears in the above-identified patent and that said Letters Patent is hereby corrected as shown below:

<u>Column 14,</u>
Line 39, please change "FIGS. 11 and 12" to -- FIGS. 8 and 9 --

Signed and Sealed this

Fifth Day of August, 2003

JAMES E. ROGAN
*Director of the United States Patent and Trademark Office*

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1:

AGTTGTAGTG GATGG                                              15

(2) INFORMATION FOR SEQ ID NO:2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:2:

```
TCAACATCAC CTACC                                                    15
```

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:3:

```
CAACATCACC TA                                                       12
```

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:4:

```
GTTGTAGTGG AT                                                       12
```

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:5:

```
AGTTGTAGTG GATGGT                                                   16
```

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:6:

```
CAACATCACC TACCA                                                    15
```

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:7:

```
GTTGTAGTGG ATGGT                                                    15
```

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:8:

```
AACATCACCT                                                          10
```

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:9:

CAACATCACC        10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:10:

ACATCACCTA        10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:11:

ACAACATCAC        10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:12:

CAACATCACA        10

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:13:

ATCACCTACC        10

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:14:

AACATCACCA        10

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:15:

CACATCACCT                                                              10

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:16:

AACATCACCG                                                              10

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:17:

TCAACATCAC                                                              10

(2) INFORMATION FOR SEQ ID NO:18:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:18:

CATCACCTAC                                                              10

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:19:

CCAACATCAC                                                              10

(2) INFORMATION FOR SEQ ID NO:20:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:20:

ACACCTACCA                                                              10

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:21:

AACATCACCC                                                              10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:22:

GCAACATCAC                                                              10

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:23:

ACATCACCTT                                                              10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:24:

AACATCACCC                                                              10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:25:

AGCACCTACC                                                              10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:26:

AAACATCACC                                                              10

(2) INFORMATION FOR SEQ ID NO:27:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (xi) SEQUENCE DESCRIPTION: SEQ ID NO:27:

ACCATCACCT                                                                 10

(2) INFORMATION FOR SEQ ID NO:28:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (xi) SEQUENCE DESCRIPTION: SEQ ID NO:28:

ACATCACCAT                                                                 10

(2) INFORMATION FOR SEQ ID NO:29:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (xi) SEQUENCE DESCRIPTION: SEQ ID NO:29:

CACCTACCAA                                                                 10

(2) INFORMATION FOR SEQ ID NO:30:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (xi) SEQUENCE DESCRIPTION: SEQ ID NO:30:

ACATCACCTC                                                                 10

(2) INFORMATION FOR SEQ ID NO:31:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (xi) SEQUENCE DESCRIPTION: SEQ ID NO:31:

ATCACCTACA                                                                 10

(2) INFORMATION FOR SEQ ID NO:32:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (xi) SEQUENCE DESCRIPTION: SEQ ID NO:32:

ACATCACCTG                                                                 10

(2) INFORMATION FOR SEQ ID NO:33:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (xi) SEQUENCE DESCRIPTION: SEQ ID NO:33:

ACACATCACC                                                          10

(2) INFORMATION FOR SEQ ID NO:34:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:34:

GAACATCACC                                                          10

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:35:

TACATCACCT                                                          10

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:36:

TAACATCACC                                                          10

(2) INFORMATION FOR SEQ ID NO:37:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:37:

CACCTACCAG                                                          10

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:38:

GACATCACCT                                                          10

(2) INFORMATION FOR SEQ ID NO:39:

(i) SEQUENCE CHARACTERISTICS:

(A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:39:

CACATCACCA                                                              10

(2) INFORMATION FOR SEQ ID NO:40:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:40:

ATCATCACCT                                                              10

(2) INFORMATION FOR SEQ ID NO:41:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:41:

ACCTACCATC                                                              10

(2) INFORMATION FOR SEQ ID NO:42:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:42:

ACAACATCAA                                                              10

(2) INFORMATION FOR SEQ ID NO:43:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:43:

CAACATCACT                                                              10

(2) INFORMATION FOR SEQ ID NO:44:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:44:

ACATCACCAA                                                              10

(2) INFORMATION FOR SEQ ID NO:45:

(i) SEQUENCE CHARACTERISTICS:
        (A) LENGTH: 10 base pairs (B) TYPE: nucleic acid
            (C) STRANDEDNESS: single
            (D) TOPOLOGY: linear (xi) SEQUENCE DESCRIPTION: SEQ ID NO:45:

CACATCACCG                                                          10

(2) INFORMATION FOR SEQ ID NO:46:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:46:

ACATCACCCT                                                          10

(2) INFORMATION FOR SEQ ID NO:47:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:47:

CACCTACCAC                                                          10

(2) INFORMATION FOR SEQ ID NO:48:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:48:

CATCACCTAA                                                          10

(2) INFORMATION FOR SEQ ID NO:49:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:49:

TCACCTACCA                                                          10

(2) INFORMATION FOR SEQ ID NO:50:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:50:

CACCTACCAT                                                          10

(2) INFORMATION FOR SEQ ID NO:51:

(i) SEQUENCE CHARACTERISTICS:
            (A) LENGTH: 10 base pairs
            (B) TYPE: nucleic acid

```
            (C) STRANDEDNESS: single
            (D) TOPOLOGY: linear (xi) SEQUENCE DESCRIPTION: SEQ ID NO:51:

CCATCACCTA                                                                    10

(2) INFORMATION FOR SEQ ID NO:52:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:52:

ACATCACCCA                                                                    10

(2) INFORMATION FOR SEQ ID NO:53:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:53:

ACATCACCGA                                                                    10

(2) INFORMATION FOR SEQ ID NO:54:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:54:

ATCAACATCA                                                                    10
```